US012551640B2

(12) United States Patent
Esplin et al.

(10) Patent No.: US 12,551,640 B2
(45) Date of Patent: Feb. 17, 2026

(54) MEDICAL GAS DELIVERY

(71) Applicant: Sleep Easy Technology LLC, South Bend, IN (US)

(72) Inventors: Anthony Esplin, South Bend, IN (US); Larry Mastrovich, Coto De Caza, CA (US); Vermon Sims Esplin, Pocatello, ID (US); Richard Ashbaugh, Pocatello, ID (US)

(73) Assignee: Sleep Easy Technology LLC, South Bend, IN (US)

( * ) Notice: Subject to any disclaimer, the term of this patent is extended or adjusted under 35 U.S.C. 154(b) by 789 days.

(21) Appl. No.: 17/741,406

(22) Filed: May 10, 2022

(65) Prior Publication Data

US 2022/0339377 A1 Oct. 27, 2022

Related U.S. Application Data

(63) Continuation-in-part of application No. 17/193,934, filed on Mar. 5, 2021, now Pat. No. 11,324,902.

(60) Provisional application No. 63/293,517, filed on Dec. 23, 2021, provisional application No. 62/985,877, filed on Mar. 5, 2020.

(51) Int. Cl.
*A61M 16/00* (2006.01)
*A61M 16/10* (2006.01)

(52) U.S. Cl.
CPC .... *A61M 16/0003* (2014.02); *A61M 16/1005* (2014.02); *A61M 2209/08* (2013.01)

(58) Field of Classification Search
CPC .......... A61M 16/0003; A61M 16/1005; A61M 2209/08; A61M 2202/0208; A61M 2230/205; A47G 9/1045
USPC ........................................................... 5/636
See application file for complete search history.

(56) References Cited

U.S. PATENT DOCUMENTS

| | | | | |
|---|---|---|---|---|
| 4,574,412 A * | 3/1986 | Smith | A47C 20/021 5/640 |
| 5,305,483 A * | 4/1994 | Watkins | A47D 15/001 5/725 |
| 5,389,037 A * | 2/1995 | Hale | A61G 10/02 55/467 |

(Continued)

FOREIGN PATENT DOCUMENTS

| | | | |
|---|---|---|---|
| CN | 209252279 U | 8/2019 | |
| CN | 209726382 U * | 12/2019 | A61M 21/00 |

(Continued)

OTHER PUBLICATIONS

USPTO acting as International Searching Authority, "International Search Report and Written Opinion," International Application No. PCT/US2022/053953, Apr. 7, 2023.

*Primary Examiner* — Justin C Mikowski
*Assistant Examiner* — George Samuel Gines
(74) *Attorney, Agent, or Firm* — DENTONS Durham Jones Pinegar

(57) ABSTRACT

A system for delivering medical gases, such as supplemental oxygen, to a subject includes a positioner and a diffuser positionable on opposite sides of a location on a surface where the subject will rest their head. The positioner may position a head and face of the subject in a desired orientation, while the diffuser may direct at least one medical gas to be delivered to the subject toward the subject's face. Methods for delivering medical gas(es) are also disclosed.

20 Claims, 7 Drawing Sheets

(56) References Cited

U.S. PATENT DOCUMENTS

| | | | | |
|---|---|---|---|---|
| 6,493,889 | B2 * | 12/2002 | Kocurek | A47G 9/0215 607/104 |
| 7,543,583 | B2 | 6/2009 | Acton | |
| 2004/0009746 | A1 * | 1/2004 | Korman | B01D 46/0032 454/284 |
| 2004/0177450 | A1 | 9/2004 | Salvatini et al. | |
| 2007/0006382 | A1 * | 1/2007 | Guez | A47G 9/10 5/636 |
| 2014/0053338 | A1 * | 2/2014 | White | A47G 9/1045 5/641 |
| 2016/0287738 | A1 * | 10/2016 | Antonino | A47G 9/1045 |
| 2021/0186235 | A1 * | 6/2021 | Zamora | A47G 9/10 |

FOREIGN PATENT DOCUMENTS

| | | | | |
|---|---|---|---|---|
| JP | 2006130200 | A | 5/2006 | |
| KR | 200419814 | Y1 * | 6/2006 | A61G 10/02 |
| WO | 2018058906 | A1 | 4/2018 | |
| WO | 2020140647 | A1 | 7/2020 | |

* cited by examiner

MEDICAL GAS DELIVERY

CROSS-REFERENCE TO RELATED APPLICATIONS

A claim for priority to the Dec. 23, 2021, filing date of U.S. Provisional Patent Application No. 63/293,517, titled MEDICAL GAS DELIVERY ("the '517 Provisional Application"), is hereby made pursuant to 35 U.S.C. § 119(e).

In addition, this application is a continuation-in-part of U.S. application Ser. No. 17/193,934, filed on Mar. 5, 2021 and titled OXYGEN DELIVERY PILLOW ("the '934 Application"), now U.S. Pat. No. 11,324,902, issued May 10, 2022, which includes a claim for priority under 35 U.S.C. § 119(e) to the Mar. 5, 2020, filing date of U.S. Provisional Patent Application No. 62/985,877, titled OXYGEN DELIVERY PILLOW ("the '877 Provisional Application").

The entire disclosures of the '517 Provisional Application, the '934 Application, and the '877 Provisional Application are hereby incorporated herein.

TECHNICAL FIELD

This disclosure relates to systems for delivering medical gases, such as supplemental oxygen, to a subject. More specifically, this disclosure relates to systems that employ pillows to deliver medical gases, including pillows and systems that are designed to be assembled with a surface of a pillow or another surface on which a subject may rest their head. Such a system includes a positioner that positions the head and face of the subject in a desired orientation and a diffuser that delivers medical gas to the face of the subject. Methods for delivering medical gases are also disclosed.

RELATED ART

A variety of health conditions may lead to the need for the delivery of medical gases, such as supplemental oxygen. Among other conditions, supplemental oxygen helps subjects who suffer from sleep apnea, acute bronchitis, asthma, heart conditions, chronic obstructive pulmonary disease (COPD), dementia, Alzheimer's disease, and other disorders achieve more stable, restful states of sleep than those subjects typically experience without supplemental oxygen. A variety of apparatuses, including conventional oxygen delivery systems, may be used to provide sleep apnea patients with supplemental oxygen as they sleep.

A conventional oxygen delivery system typically includes an oxygen source (e.g., an oxygen concentrator, an oxygen tank, liquid oxygen, etc.), tubing, and a nasal cannula that delivers oxygen from the oxygen concentrator to a subject's nose. An oxygen concentrator concentrates oxygen from the air, providing air with an above-ambient concentration of oxygen, which is also referred to herein as "supplemental oxygen" for the sake of simplicity. The oxygen source delivers the supplemental oxygen to and through tubing to the nasal cannula. The nasal cannula has a configuration that enables it to be secured beneath a subject's nose in an orientation that directs the pressurized supplemental oxygen into the subject's nose. It is up to the patient to breathe in to access that oxygen from the nasal cannula. If the patient is a mouth breather, as over 70% of people are when they sleep, the concentrated oxygen is not inhaled. Nasal cannulas may also be ineffective for delivering supplemental oxygen to subjects who suffer from upper respiratory tract infections (e.g., a common cold, influenza, sinus infections, etc.) and to subjects who suffer from nasal abnormalities (e.g., a deviated septum, etc.).

The use of a nasal cannula can be uncomfortable and irritating. The presence of the nasal cannula beneath the subject's nose may be bothersome (e.g., it may lead to nose bleeds when the air is dry, such as during wintertime, etc.). In addition, the delivery of supplemental oxygen into a subject's nose has a tendency to dry out the subject's nasal membranes, which may make the nasal cannula even more bothersome. The discomfort a subject experiences while wearing a nasal cannula and while the nasal cannula delivers regulated, supplemental oxygen to the subject's nose may lead to removal of the nasal cannula—either intentionally or unintentionally—as the subject tries to sleep. When the nasal cannula is removed or the subject breathes through their mouth, however, the subject no longer receives supplemental oxygen, which may cause the same problem the supplemental oxygen is intended to address (e.g., fitful, interrupted sleep for hypoxia patients, etc.).

SUMMARY

An embodiment of a medical gas delivery system of this disclosure may include a diffuser and a positioner.

The diffuser may include a base that supports the diffuser on a surface (e.g., a surface on which a subject rests their head, such as a pillow, etc.), walls that define a recess, an inlet at one end of the receptacle, and a delivery face at an opposite end of the recess. A gas delivery tube may couple to the diffuser adjacent to the inlet. The walls of the diffuser may taper outwardly from the side of the diffuser on which the inlet is located to the side of the diffuser on which the delivery face is located. The walls of the diffuser may impart the diffuser with a size and a shape that enable gas to be delivered efficiently and effectively to the face of a subject. Use of the diffuser includes providing gas flow from a source, through the gas delivery tube, through the inlet, into the recess, and out of the delivery face.

Optionally, an inlet of the diffuser may increase turbulence in gases that are delivered by the diffuser, which may facilitate the creation of a "gas cloud" for inhalation by a subject. Such an inlet may include a baffle located within the recess of the diffuser, over a channel and/or an aperture the inlet. More specifically, the baffle may be positioned within a flow path defined by the inlet. A configuration (e.g., a shape, dimensions, etc.) and a position of the baffle may cause gas that flows into the recess to flow around the baffle and then toward and through the delivery face, albeit less forcefully and more diffuse than if the gas were to flow unimpeded through the recess. In some embodiments, the baffle may be removable from the recess and replaceable within the recess.

The positioner may include a base that supports the head positioner on the surface, as well as an orienting surface that receives a back of a subject's head in a manner that orients the subject's head on the surface and positions the subject's face toward the delivery face of the diffuser.

One or both of the diffuser and the positioner may include a coupler, or an anchor. A coupler may hold the base of its respective component (i.e., the diffuser or the positioner) in place on the surface that supports the component. In embodiments where the surface comprises a surface of a pillow or another cushion, the coupler may comprise a strap that extends around the pillow or other cushion to secure the component to it. Alternatively, the coupler may comprise a so-called "touch fastener" (e.g., the hook elements of Velcro, etc.) that engages another touch fastener or a fabric (e.g., a soft, fuzzy fabric that comprises the loop elements of Velcro, etc.) on the surface (e.g., a pillowcase on a pillow, etc.). As another alternative, the coupler may comprise a pocket associated with (e.g., on, in, etc.) the surface.

The medical gas delivery system may also include a cover. In some embodiments, including those where surface comprises a surface of a pillow or another cushion, the cover may comprise a pillowcase. The cover may include a vent therethrough, which may be positionable over or adjacent to the delivery face of the diffuser to accommodate gas that flows from the delivery face of the diffuser. A shape of the vent may enable it to accommodate a plurality of different positions of the diffuser on the surface.

A medical gas may be delivered to a subject with such a medical gas delivery system by arranging the medical gas delivery system on a surface (e.g., a pillow, another cushion, etc.) where the subject will rest their head. The positioner is positioned at a first location on the surface, adjacent to a second location on the surface, where the subject's head will rest. The orienting surface of the positioner, which may have a shape that will receive a back of the head of the subject, may face the second location, enabling the orienting surface to orient the head of the subject sideways over the second location on the surface. The diffuser may be positioned at a third location on the surface, adjacent to the second location and on an opposite side of the second location from the first location. The delivery face of the diffuser may be oriented toward the second location. The delivery face may be oriented at an angle to the surface (e.g., an acute angle, etc.), which may enable the gas to be more effectively and/or efficiently delivered to the face of the subject. One or both of the positioner and the diffuser may be secured in place relative to the surface (e.g., over the surface, to the surface, within a pocket associated with the surface, etc.).

In some embodiments, a cover may be positioned over the positioner, the diffuser, and the surface. Positioning the cover may include positioning a vent through the cover over or adjacent to the delivery face of the diffuser to enable gas to flow freely from the delivery face of the diffuser to a face of the subject.

A subject's head may be placed on the second location of the surface, with the back of the head placed against the orienting surface of the positioner, a side of the head placed against the second location, and a face of the subject oriented toward the delivery face of the diffuser. As the subject's head is placed on the second location of the surface, the delivery face of the diffuser may tilt downward in a manner that deceases a distance between the delivery face and the second location on the surface, as well as a distance between the subject's face and the delivery face. If desired, the position of one or both of the positioner and the diffuser may be adjusted (e.g., moved laterally, etc.) to increase the subject's comfort, optimize the efficiency with which the medical gas delivery systems delivers the gas to the subject, or the like.

With the subject's head positioned on the surface, the gas may be delivered through the delivery face of the diffuser to the face of the subject.

Other aspects of the disclosed subject matter, as well as features and advantages of various aspects of the disclosed subject matter, should be apparent to those of ordinary skill in the art through consideration of the ensuing description, the accompanying drawings, and the appended claims.

DETAILED DESCRIPTION

Figure 1:
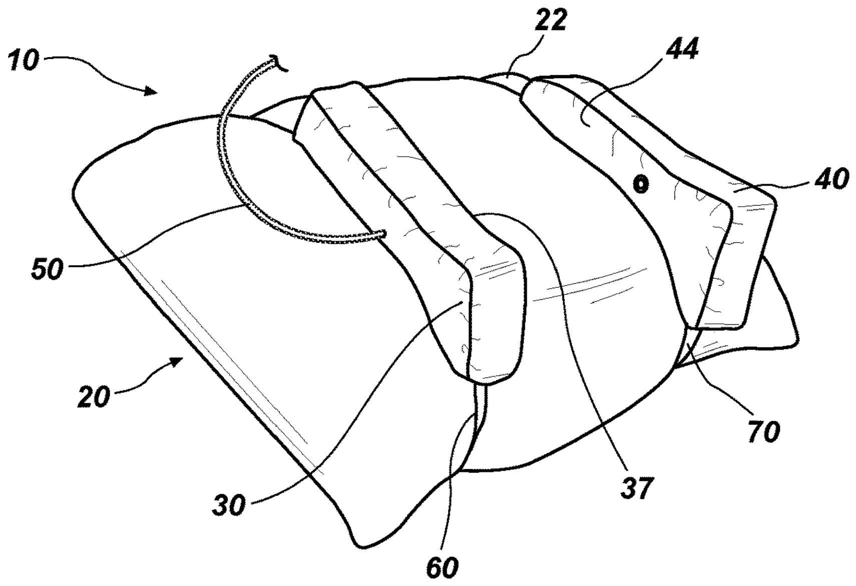
FIG. 1 is a perspective view of an embodiment of medical gas delivery system according to this disclosure.

FIG. 1 illustrates an embodiment of a medical gas delivery system 10 according to this disclosure. The medical gas delivery system 10 is configured to be placed upon a surface 22 upon which a subject's head will rest, such as a surface 22 of a pillow 20 of another cushion.

The medical gas delivery system 10 includes a diffuser 30 and a positioner 40. The diffuser 30 may be positioned over the surface 22 at a location and in an orientation that will enable it to direct one or more medical gases (e.g., supplemental oxygen, air, etc.) to a desired location over the surface 22, such as a location where a subject's face will be positioned. The positioner 40 may be positioned over the surface 22 at a location and in an orientation that will enable it to orient the subject's head and face toward the diffuser 30. As illustrated, the positioner 40 may be spaced apart from the diffuser 30 by a sufficient distance to accommodate the subject's head.

p A diffuser anchor 60, which may also be referred to as a diffuser coupler or more simply, as a coupler, may secure the diffuser 30 in place over the surface 22 in a desired location and in a desired orientation. A positioner anchor 70, which may also be referred to as a positioner coupler or more simply, as a coupler, may secure the positioner 40 in place over the surface 22 in a desired location and in a desired orientation. Without limitation, the diffuser anchor 60 and/or the positioner anchor 70 may comprise a strap, as depicted. Alternatively, the diffuser anchor 60 and/or the positioner anchor 70 may comprise a so-called touch fastener (e.g., a hook portion of a Velcro fastener, which may engage loops of a fabric that defines the surface 22, etc.), an adhesive material, or any other suitable anchor.

As an alternative to the aforementioned diffuser anchor 60 and positioner anchor 70, a medical gas delivery system 10 according to this disclosure may include a cover (not shown), such as a pillowcase, that holds, or anchors, the diffuser 30 and the positioner 40 in place over the surface 22. Such a cover may include pockets that are at least partially defined by vents (e.g., openings through the fabric of the cover, a mesh panel in the fabric, another type of panel that allows air to flow therethrough without restricting airflow, etc.). As another option, a cover, such as a pillowcase, may be used in conjunction with other anchors to accommodate a variety of different placements of the diffuser 30 and positioner 40 while increasing comfort for the subject and providing for unrestricted flow of the medical gas to the subject's face.

In addition to the diffuser 30 and the positioner 40, the medical gas delivery system 10 may include a conduit, which may be referred to as a "gas delivery tube 50," that transports a medical gas from a source (not shown) to the diffuser 30.

In some embodiments, the medical gas delivery system 10 may also include a spacer (not shown), which facilitates positioning of the diffuser 30 and the positioner 40 relative to each other.

In some embodiments, the diffuser 30 may comprise a block of a cushioning foam through which the gas delivery tube 50 may extend. The diffuser 30 may have the shape of a rectangular prism, or it may be shaped as an oblique triangle with a delivery face 37 that creates a tent-like well over the surface 22 to trap and, thus, obstruct the dissipation of the medical gas and, thus, improve the efficiency with which the medical gas may be delivered to a subject's face.

Figure 2:
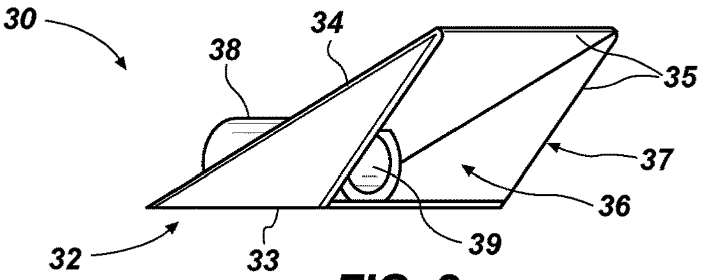
FIG. 2 is a front perspective view of an embodiment of a diffuser of the medical gas delivery system of FIG. 1.
Figure 3:
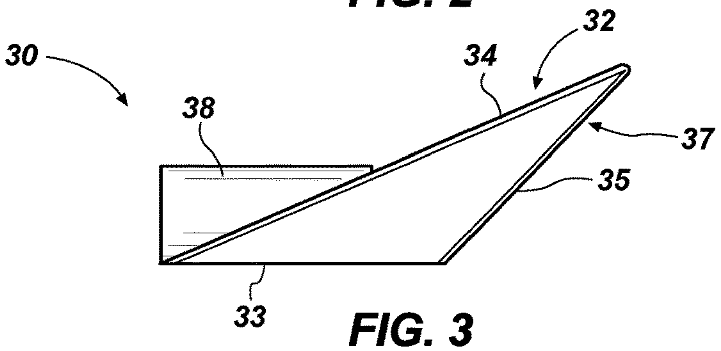
FIG. 3 is a side view of the embodiment of diffuser shown in FIG. 2.
Figure 4:
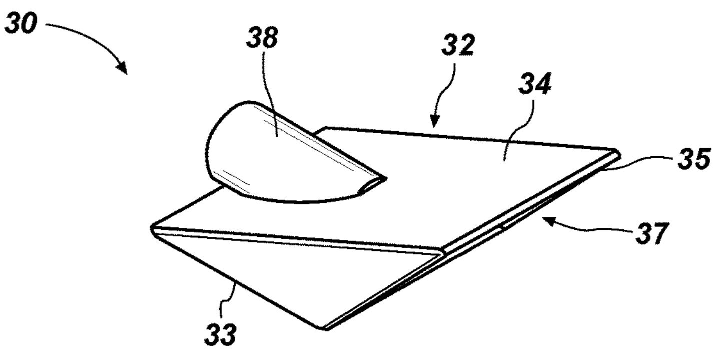
FIG. 4 is a top perspective view of the embodiment of diffuser shown in FIG. 2.
Figure 5:
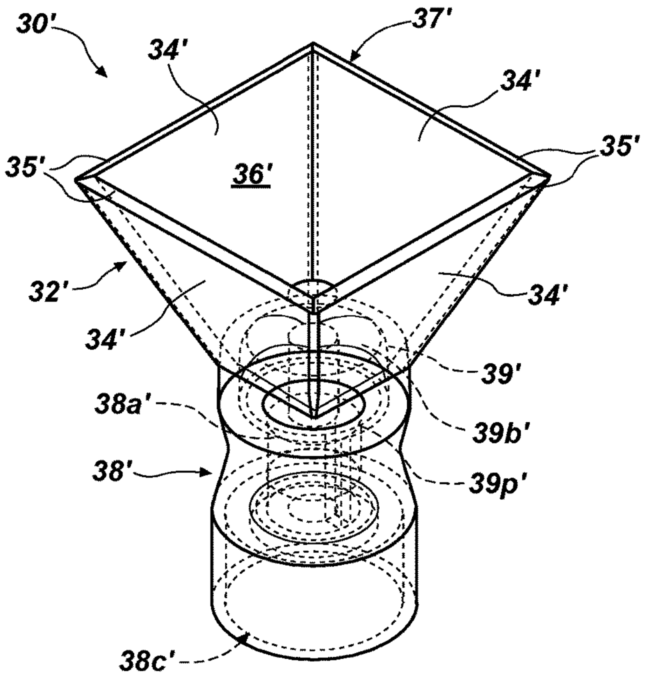
FIG. 5 is an isometric view of another embodiment of diffuser that may be used in a medical gas delivery system.
Figure 6:
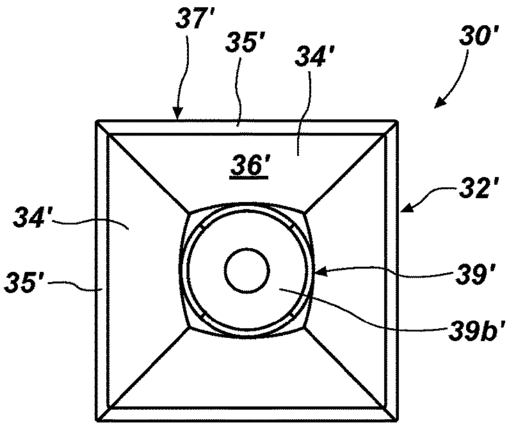
FIG. 6 is a top, or distal side, plan view of the embodiment of the diffuser shown in FIG. 5.
Figure 7:
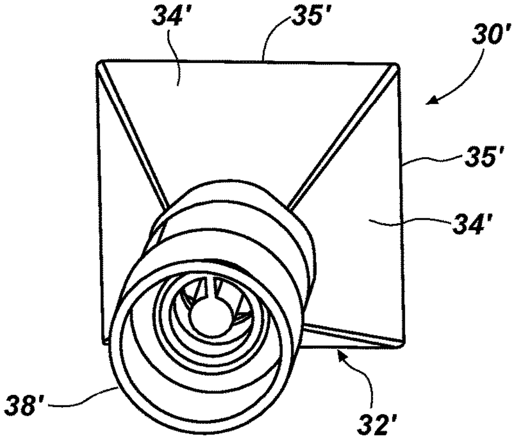
FIG. 7 is a bottom, or proximal side, perspective view of the embodiment of the diffuser shown in FIG. 5.
Figure 8:
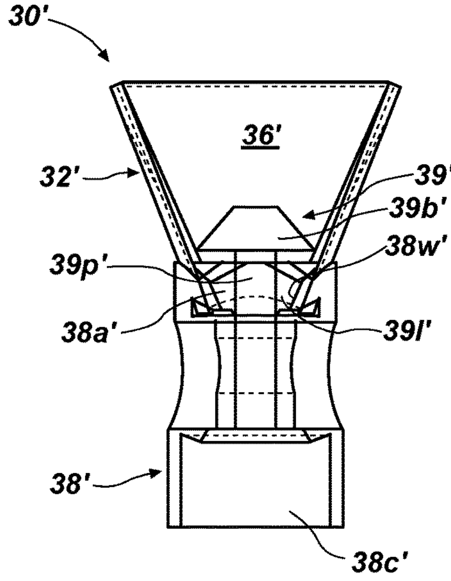
FIG. 8 is a cross-sectional representation of the embodiment of the diffuser shown in FIG. 5.

With reference to FIGS. 2-4, another specific embodiment of a diffuser 30 is depicted. The diffuser 30 includes a body 32, a recess 36, a delivery face 37, and an inlet 38. The body 32 includes a base 33, a rear wall 34 that extends upward from a rear of the base 33, and front edges 35 that extend upward from a front of the base 33. The body 32 defines the recess 36. The recess 36 opens to the delivery face 37, which is defined by the front edges 35 of the body 32. The inlet 38 may be positioned on the rear wall 34 of the body 32. The inlet 38 may have a configuration that enables it to couple with and receive a medical gas from the gas delivery tube 50. A channel 39 extends through the inlet 38, the rear wall 34, and into the recess 36 of the diffuser 30, enabling the transport of medical gas into the recess 36. The medical gas may flow out of the recess 36 through the delivery face 37.

In some embodiments, the delivery face 37 of the diffuser 30 may be oriented at an obtuse angle to the base 33 of the body 32 of the diffuser 30. The delivery face 37 may be oriented to define an acute angle with the surface 22 on which the diffuser 30 is placed. The angle between the surface 22 and the delivery face 37 may at least partially accommodate a subject's face when the subject's head is placed on the surface 22, toward the delivery face 37 of the diffuser 30, which may cause a portion of the diffuser 30 to extend over the surface 22 or even over a portion the subject's face in a manner that (further) traps air and any medical gas mixed therewith and, thus, (further) limits the rate at which the air and any medical gas mixed therewith can diffuse upwardly, which may (further) improve the efficiency with which the diffuser 30 delivers medical gas to the subject's face. In embodiments where the surface 22 on which the diffuser 30 is placed gives way (e.g., concavely bows, is indented, etc.) when the subject's head is placed thereon, the extent to which the portion of the diffuser 30 extends over the surface 22 may increase, which may further improve the efficiency with which medical gas is delivered to the subject's face.

As seen in FIGS. 5-8, another embodiment of diffuser 30' is depicted. The diffuser 30' includes a body 32', a recess 36', a delivery face 37', an inlet 38', and a baffle 39'. The inlet 38' is located at a proximal side of the diffuser 30'. The body 32' includes walls 34' that extend outward distally from the inlet 38' to define the recess 36', with outer edges 35' of the walls 34' defining delivery face 37' at a distal side of the diffuser 30'. The recess 36' opens to the delivery face 37'.

The inlet 38' may have a configuration that enables it to couple with and receive a medical gas from the gas delivery tube 50 (FIG. 1). The inlet 38' may include a channel *38c'* that extends through a proximal side of the inlet 38'. The inlet 38' may also include an aperture *38a'*, which may be located at a distal end of the channel *38c'*. The channel *38c'* may have a configuration that enables it to receive and, optionally, couple to a distal end of the gas delivery tube 50 (FIG. 1).

The baffle 39' may be positionable (e.g., in embodiments where the baffle 39' is removable and/or replaceable, etc.) or positioned over a distal side of the aperture *38a'* of the inlet 38. The baffle 39' includes a body *39b'* and may include a post *39p'*, which may extend from a proximal side of the body *39b'*. The post *39p'* may hold the body *39b'* of the baffle 39' in place over the aperture *38a'* of the inlet 38; more specifically, the post *39p'* may extend partially into the aperture *38a'*, with a lateral extension *39l'* from the post *39p'* securing the post *39p'* in place relative to a wall *38w'* of the aperture *38a'*. A distance across the body *39b'* (e.g., an outer diameter of the body *39b'*, etc.) may exceed a distance across the aperture *38a'* (e.g., an inner diameter of the aperture *38a'*, etc.).

Gas entering the inlet 38' may be able to flow into the aperture *38a'*, around the post *39p'*, and into the recess 36', where the body *39b'* of the baffle 39' disrupts flow of the gas. A shape of the body *39b'* may be tailored to disrupt the flow of gas into the recess 36' in a desired manner. In the depicted embodiment, the body *39b'* has a configuration with a mushroom-like appearance, in which its distal side is larger than its proximal side and its proximally facing surfaces taper, or even curve, to its proximal side.

Figure 9:
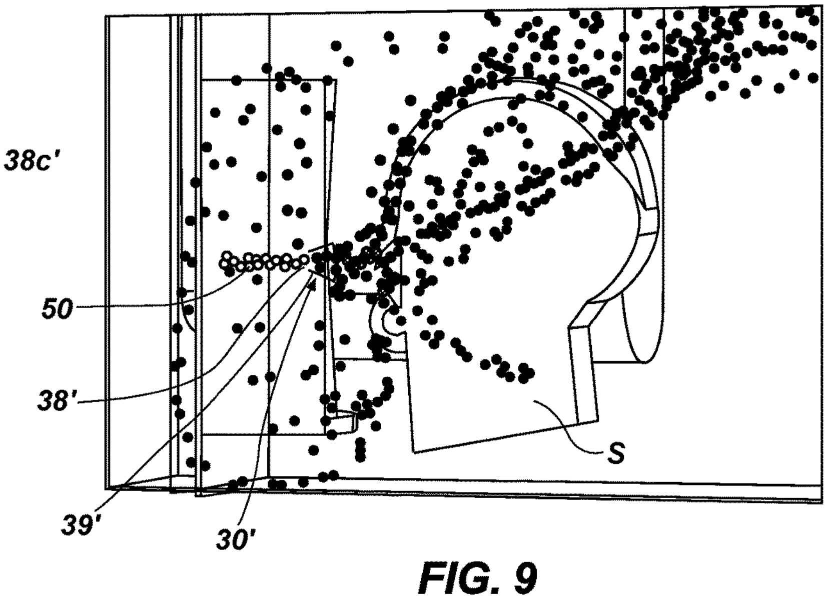
FIG. 9 provides a representation of flow simulation through the embodiment of the diffuser shown in FIGS. 5-8.
Figure 10:
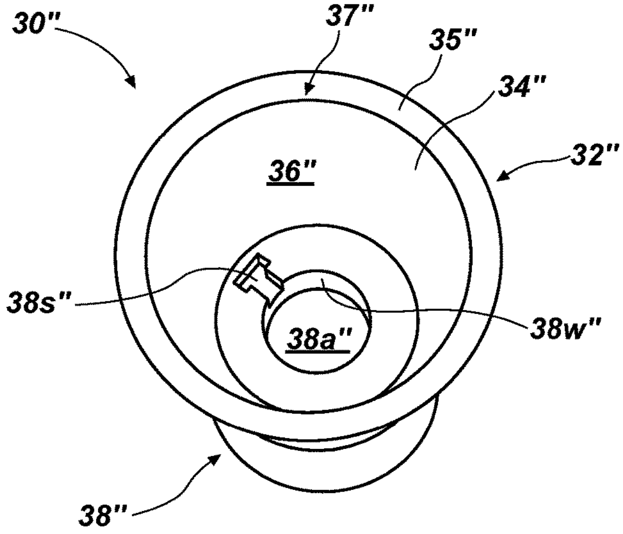
FIG. 10 is a top, or distal side, isometric view of yet another embodiment of a diffuser that may be used in a medical gas delivery system.
Figure 11:
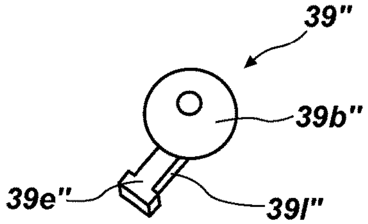
FIG. 11 is a top, or distal side, isometric view of an embodiment of a baffle that may be assembled over an inlet of the embodiment of the diffuser shown in FIG. 10.
Figure 12:
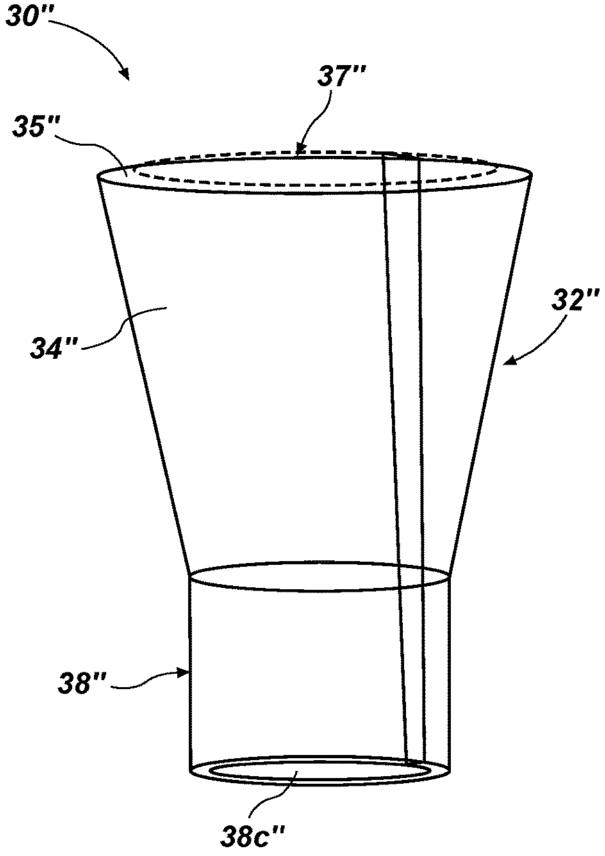
FIG. 12 is a side view of the embodiment of the diffuser shown in FIG. 10.
Figure 13:
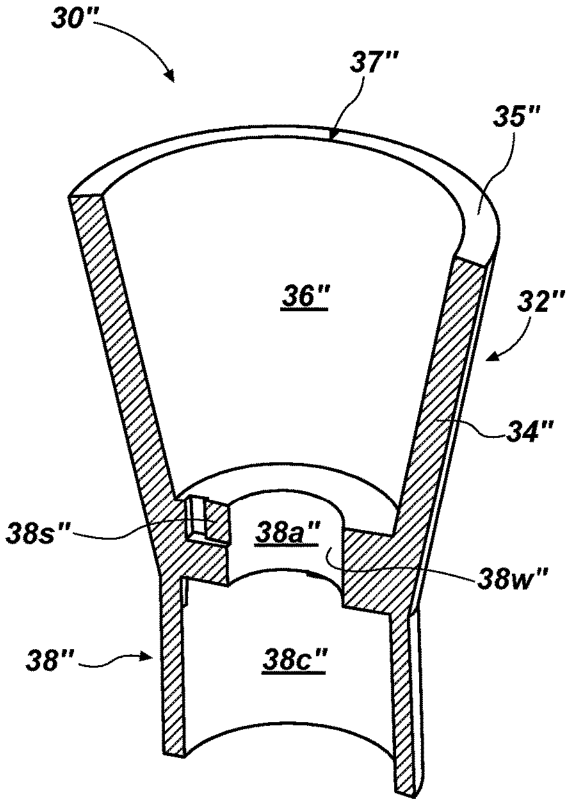
FIG. 13 is a cutaway view of the embodiment of the diffuser shown in FIG. 10.

FIG. 9 is a diagram that provides a representation of the manner in which the baffle 39' disrupts and diffuses gas flow delivered to a subject S through a gas delivery tube 50 to and through the embodiment of diffuser 30' shown in FIGS. 5-8, with the dots representing gas molecules (e.g., $O_2$, etc.).

Another embodiment of diffuser 30" is shown in FIGS. 10-13. The diffuser 30" includes a body 32", a recess 36", a delivery face 37", an inlet 38", and a baffle 39". The inlet 38" is located at a proximal side of the diffuser 30". The body 32" includes a wall 34" that extends outward distally from the inlet 38" to define the recess 36", with an outer edge 35" of the wall 34" defining the delivery face 37" at a distal side of the diffuser 30". The recess 36" opens to the delivery face 37".

The inlet 38" may include a channel **38*c*" that extends through a proximal side of the inlet 38'. The channel 38*c*" may have a configuration that enables it to receive and, optionally, couple to a distal end of the gas delivery tube 50 (FIG. 1). The inlet 38" may also include an aperture 38*a*" at a distal end of the channel 38*c*"**.

A baffle engagement slot **38*s*" may be formed in the inlet 38". The baffle engagement slot 38*s*" may be continuous with and, thus, open to a side of the aperture 38*a*". A configuration of the baffle engagement slot 38*s*" may enable it to receive and engage a corresponding diffuser engager 39*e*" of the baffle 39". The configuration of the baffle engagement slot 38*s*" may enable it to receive the diffuser engager 39*e*" in a manner that ensures the baffle 39" is properly positioned within the recess 36" of the diffuser 30"**.

The baffle 39" may be removably positioned over a distal side of the aperture **38*a*" of the inlet 38" of the diffuser 30". The baffle 39" includes a body 39*b*". A post 39*p*" extends from a proximal side of the body 39*b*" of the baffle 39". A lateral extension 39*l*" from the post 39*p*" connects the diffuser engager 39*e*" to the post 39*p*". The diffuser engager 39*e*" is receivable by the baffle engagement slot 38*s*" of the inlet 38" and, thus, holds the baffle 39" in place relative to a wall 38*w*" of the aperture 38*a*" of the inlet 38", with body 39*b*" of the baffle 39" being located over the aperture 38*a*". A distance across the body 39*b*" (e.g., an outer diameter of the body 39*b*", etc.) may exceed a distance across the aperture 38*a*" (e.g., an inner diameter of the aperture 38*a*", etc.). The post 39*p*" may extend partially into the aperture 38*a*"**.

Gas entering the inlet 38" may be able to flow into the aperture **38*a*", around the post 39*p*", and into the recess 36", where the body 39*b*" of the baffle 39" disrupts flow of the gas. A shape of the body 39*b*" may be tailored to disrupt the flow of gas into the recess 36" in a desired manner. In the depicted embodiment, the body 39*b*"** has a configuration with a mushroom-like appearance, in which its distal side is larger than its proximal side and its proximally facing surfaces taper, or even curve, to its proximal side.

With returned reference to FIG. 1, the positioner 40 may include a base 42 and an orienting surface 44. The base 42 may face the surface 22 over which the positioner 40 is positioned. The orienting surface 44, which extends upwardly from the base 42, may be oriented on the surface 22 such that the orienting surface 44 faces the diffuser 30. The orienting surface 44 has a shape that enables it to receives the back of the subject's head and to stably orient the subject's head such that the subject's face will face the delivery face 37 (FIGS. 2-4) of the diffuser 30. With limitation, the positioner 40 may comprise a shaped block of foam or another cushioning material with sufficient density to support and stably hold the subject's head in a desired orientation.

Figure 14:
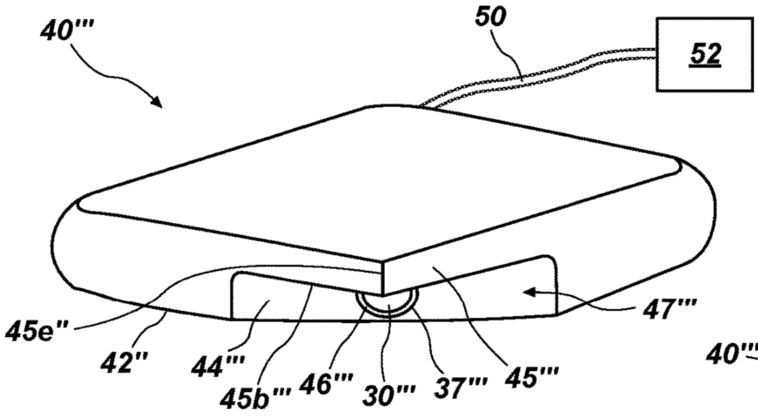
FIGS. 14 and 15 are isometric views of an embodiment of a positioner that carries a diffuser, such as the embodiment of the diffuser shown in FIGS. 5-8 or the embodiment of the diffuser shown in FIGS. 10-13.
Figure 15:
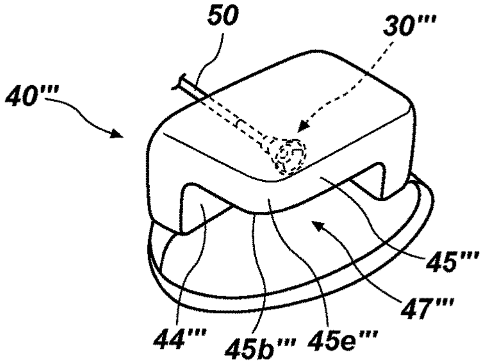
Figure 16:
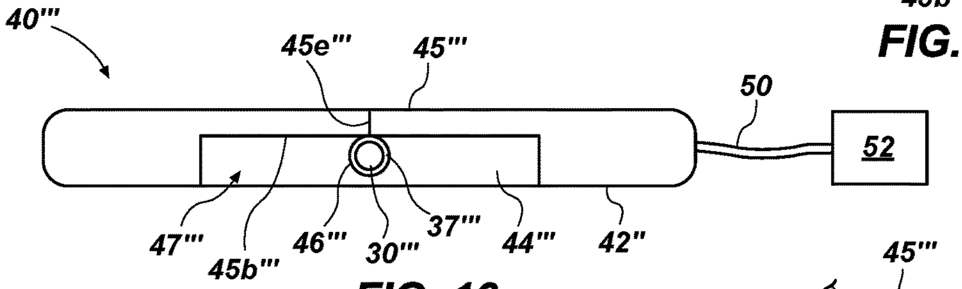
FIG. 16 is a side view of the embodiment of the positioner shown in FIGS. 14 and 15.

Referring now to FIGS. 14-16, an embodiment of a positioner 40'" that carries a diffuser 30'" is depicted. The positioner 40'" may be configured similarly to the positioner 40 shown in and described in reference to FIG. 1. The positioner 40'" may include a base 42'" and a lateral surface 44'" with configurations that enable them to perform the same functions as the base 42 and orienting surface 44 of the embodiment of the positioner 40 shown in FIG. 1. In addition, the lateral surface 44'" may include a receptacle 46'" for the diffuser 30'". A configuration of the receptacle 46'" may enable it to orient the diffuser 30'" in a manner that causes gas to flow laterally or at a somewhat downward angle, from the diffuser 30'" through a side, or the lateral surface 44", of the positioner 40'". As illustrated, the receptacle 46'" may carry the diffuser 30'", which may comprise a diffuser according to this disclosure, which may in turn receive a medical gas from a medical gas source 52 through a gas delivery tube 50.

The positioner 40'" may include a cushion flap 45'" protruding from an upper portion of the lateral surface 44'" and extending over the lateral surface 44'". Thus, the cushion flap 45'" may extend over, or overhang, the receptacle 46'" and any diffuser 30'" therein. The cushion flap 45'" may have a configuration that enables it to collapse (e.g., over the delivery face 37'" of the diffuser 30'", etc.) to comfortably support a subject's head while minimizing any discomfort that might otherwise be caused as the subject's head rests on the diffuser 30'". In addition, the cushion flap 45'" may automatically return to its overhanging orientation when the subject's head is removed from it, exposing the diffuser 30'" and its delivery face 37'" so the flow of gas therefrom is unobstructed.

Figure 17:
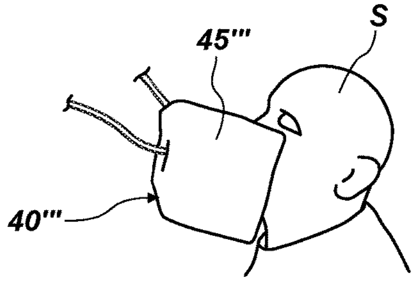
FIG. 17 illustrates use of the embodiment of the positioner shown in FIGS. 14-16 to supply supplemental gas to a subject.

The cushion flap 45'" of the positioner 40'" may also be positioned over a portion of a face of a subject S (e.g., the subject S's mouth and/or nose, etc.) when the diffuser 30'" carried by the positioner 40'" is used to supply a medical gas to the individual, as shown in FIG. 17. An orientation (e.g., slightly raised, etc.) and/or a shape (e.g., concavely bowed, etc.) of the cushion flap 45'" may provide a pocket 47'" that can comfortably receive a portion of the face of a subject S. For example, an outer edge of the cushion flap 45'" may be slightly raised. As another example, the cushion flap 45'" may be bowed. As yet another example, a lower surface **45*b*'" of the cushion flap 45'" may be concavely bowed. In still another example, a thickness of the cushion flap 45'" may gradually decrease from the location where it extends from the orienting surface 44'" to its outer edge 45*e*'". The pocket 47'" created by the cushion flap 45'" may trap air and any medical gas mixed therewith, which may prevent the air and any medical gas mixed therewith from diffusing before the subject S can inhale it, which may enhance the efficiency with which the diffuser 30'"** delivers medical gas to the face of the subject S.

Figure 18:
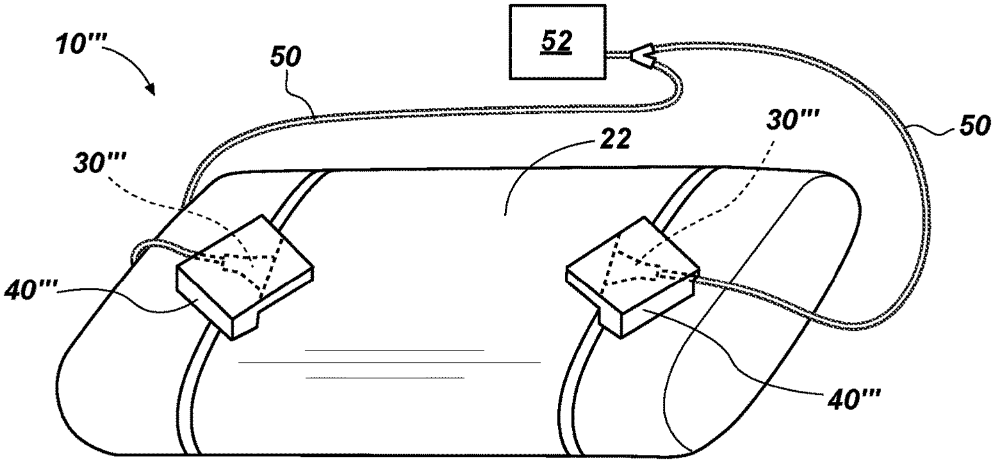
FIG. 18 provides a representation of an embodiment of a medical gas delivery system that includes two positioners that carry diffusers, such as the embodiment of the positioner shown in FIGS. 14-16.

FIG. 18 illustrates an embodiment of a medical gas delivery system 10'" that includes two positioners 40'" that carry diffusers 30'". Gas delivery tubes 50 extend between a medical gas source 52 and the diffusers 30'" to enable medical gas to flow from the medical gas source 52 to and through the diffusers 30'". The positioners 40'" may be positioned at spaced apart locations on a surface 22. As illustrated, the positioners 40'" may be spaced apart from each other by a sufficient distance to accommodate a subject's head. A location and an orientation of each positioner 40'" may enable the diffuser 30'" carried by each positioner 40'" to direct one or more medical gases (e.g., supplemental oxygen, air, etc.) to a desired location over the surface 22 between the positioners 40'", such as a location where the subject's face may be positioned. In addition, a location and an orientation of each positioner 40'" may enable it to orient the subject's head and face toward the diffuser 30'" carried by the opposite positioner 40'".

In such a medical gas delivery system 10''', the flow of medical gas may be the same or about the same as the flow if the medical gas were to be delivered through a nasal cannula (e.g., about 2 L/min., about 1-4 L/min., about 1-6 L/min, any value within the aforementioned ranges, etc.), but split between the diffusers 30''' (e.g., about 1 L/min per diffuser 30''', about 0.5-2 L/min., about 0.5-3 L/min, any value within the aforementioned ranges, etc.). Despite the split flow of medical gas, a configuration of each diffuser 30''' (e.g., the presence of a baffle 39', 39'' in diffuser 30', 30'', respectively, etc.) may insure that the fixed inspired (FI) content of the gas (e.g., $FIO_2$, etc.) is the same as if the medical gas were delivered through a nasal cannula (e.g., $FIO_2$ content may be about 24% to about 44%, by volume, etc.). Thus, regardless of which side, or diffuser 30''' a subject's face faces, the subject may receive approximately the same concentration of the medical gas as they would have if they instead used a much less comfortable nasal cannula.

Figure 19:
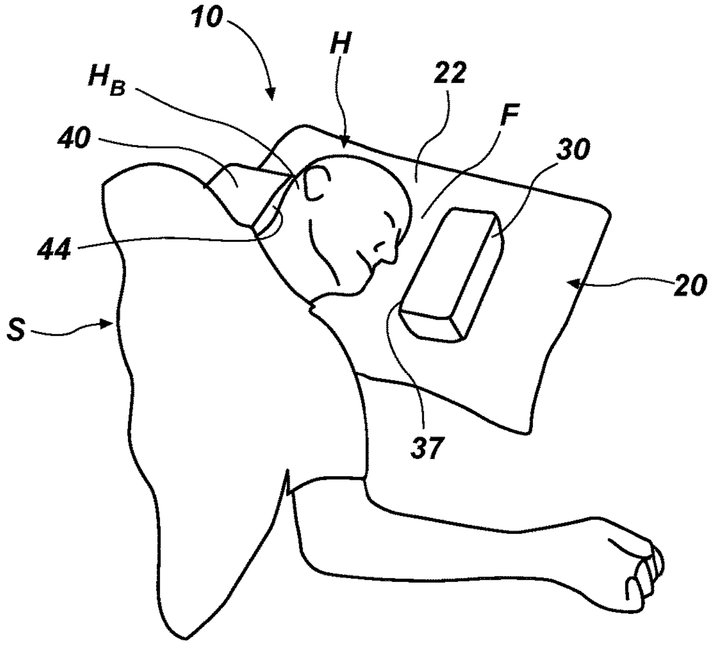
FIG. 19 depicts an embodiment of use of an embodiment of the embodiment of the medical gas delivery system shown in FIGS. 1-4.
Figure 20:
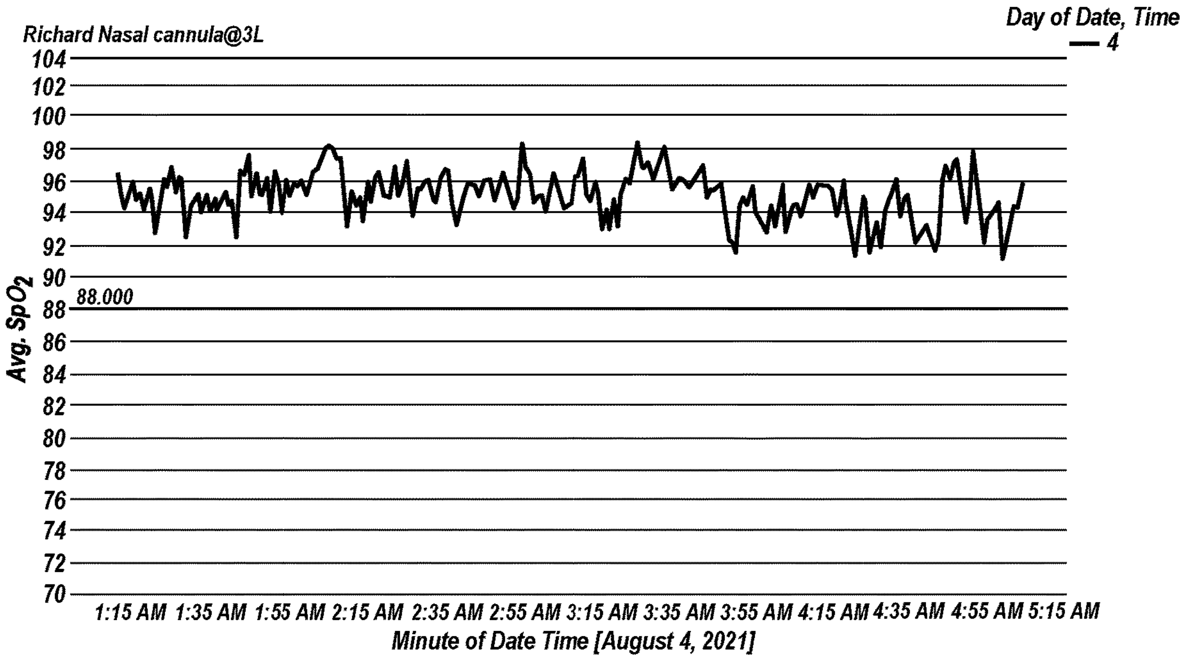
FIG. 20 is a graph showing the blood oxygen saturation ($SpO_2$) of a subject receiving supplemental oxygen through a nasal cannula at a flow rate of 3 L/min.
Figure 21:
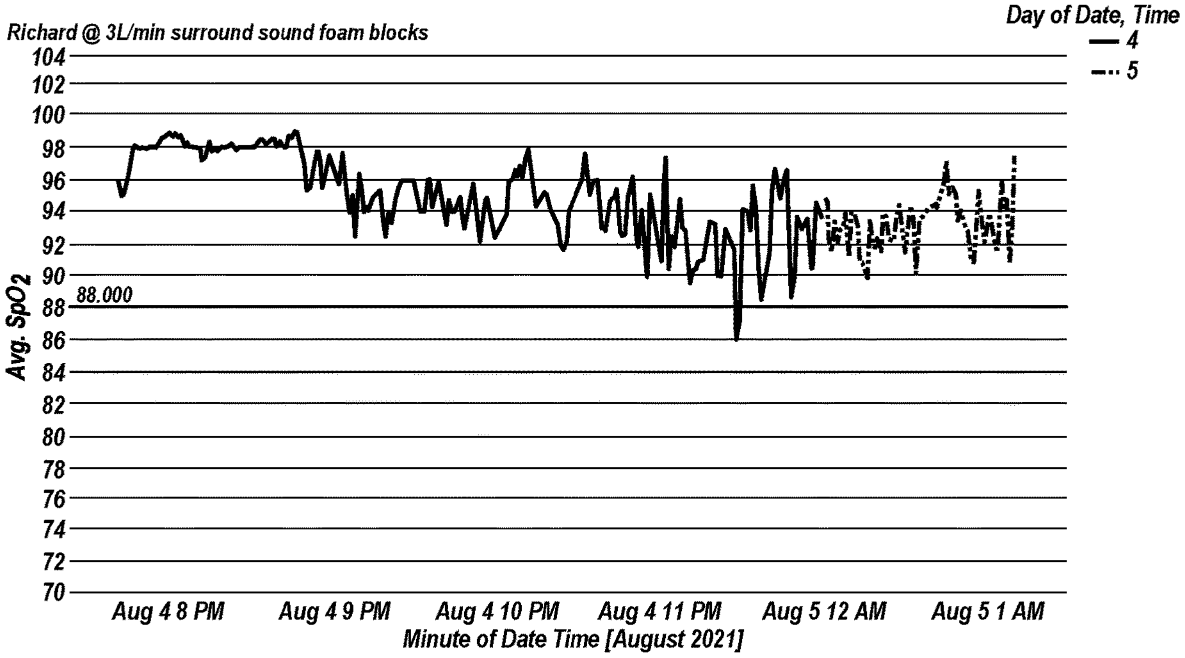
FIGS. 21-23 are graphs showing the blood oxygen saturation of the same subject on three successive nights, with the embodiment of the medical gas delivery system depicted by FIG. 19 delivering the supplemental oxygen at a flow rate of 3 L/min.
Figure 22:
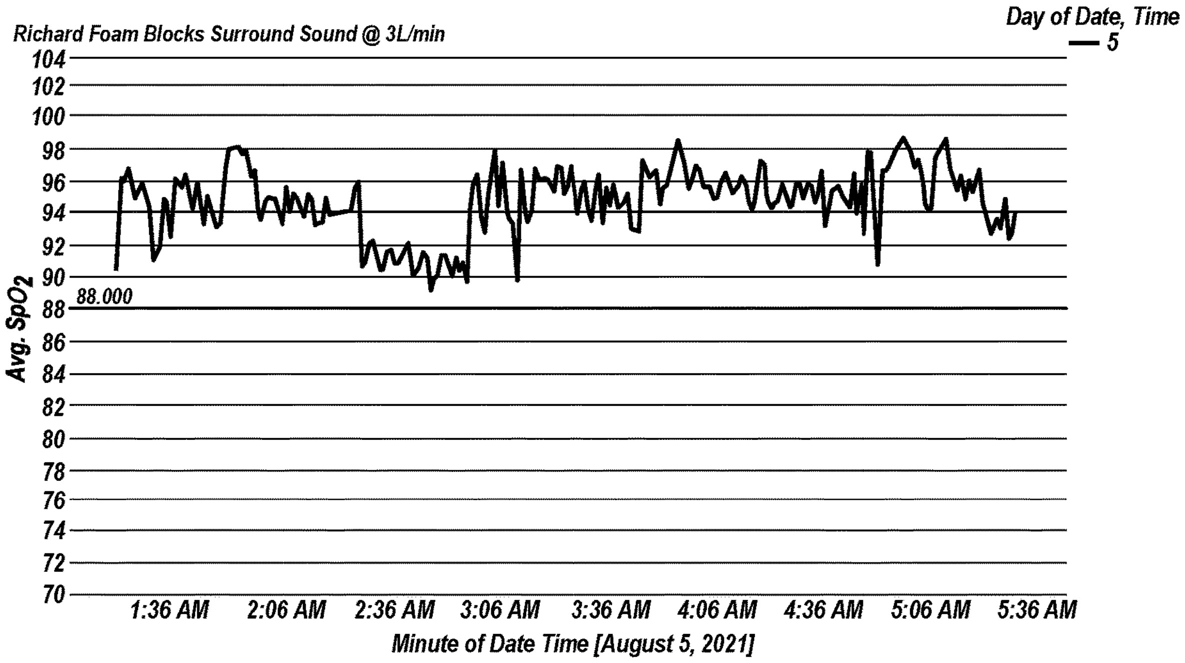
Figure 23:
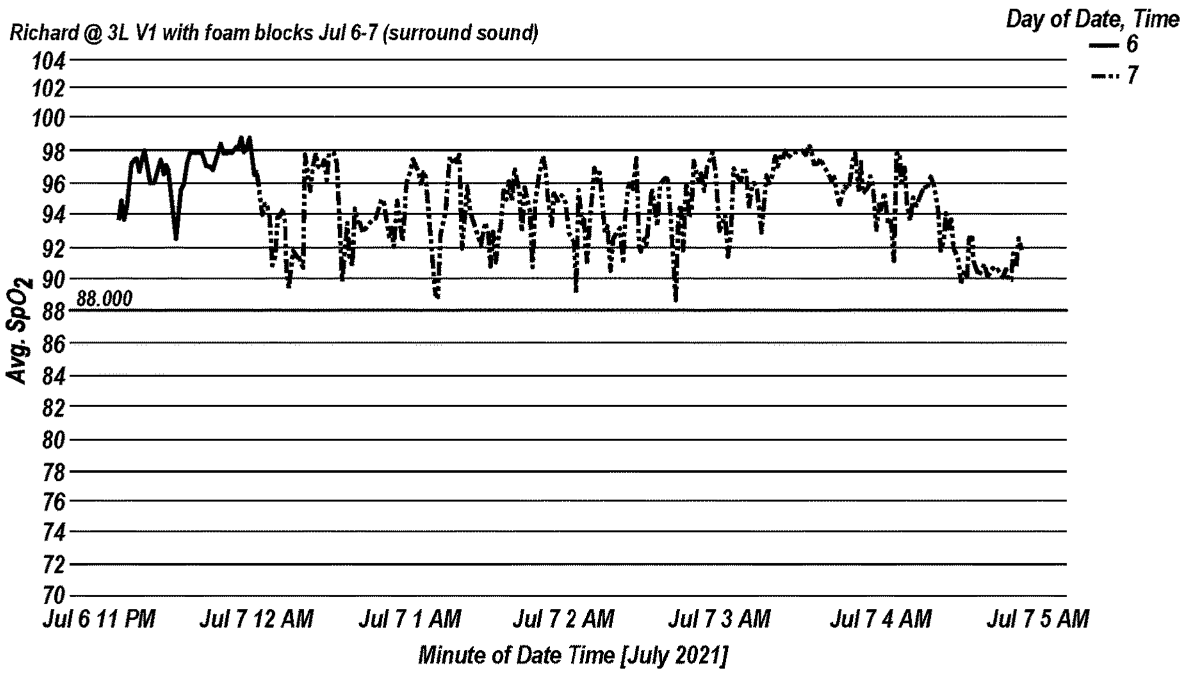

Turning now to FIG. 19, an embodiment of use of a medical gas delivery system 10 is depicted. The method is also applicable to any other embodiment of medical gas delivery system according to this disclosure, including the medical gas delivery system 10''' shown in FIG. 18. As illustrated, a diffuser 30 and a positioner 40 have been positioned over the surface 22 of a pillow 20. The back $H_B$ of a subject S's head H rests against the orienting surface 44 of the positioner 40, while the delivery face 37 of the diffuser 30 faces the subject S's face F. To provide a baseline, the subject S's blood oxygen saturation ($SpO^2$) was measured while the subject S received supplemental oxygen at a flow rate of 3 L/min. over a first night, as depicted by the graph of FIG. 20. On three subsequent nights, the subject's blood oxygen saturation was again measured while the subject S slept using the system shown in FIG. 19, which also delivered supplemental oxygen at a flow rate of 3 L/min, as depicted by the graphs of FIGS. 21-23. As can be seen by comparing the graphs of FIGS. 21-23 (i.e., average $SpO_2$ of greater than 94% each night) to the graph of FIG. 20 (i.e., average $SpO_2$ of about 94.5%), the medical gas delivery system 10 delivered the supplemental oxygen with an efficiency equivalent to that of a nasal cannula.

Although this disclosure and the accompanying drawings provide many specifics, they should not be construed as limiting the scopes of any of the appended claims, but merely as providing information pertinent to some specific embodiments that may fall within the scopes of the appended claims. Features from different embodiments may be employed in combination. In addition, the scopes of the appended claims may encompass other embodiments. All additions to, deletions from, and modifications of the disclosed subject matter that fall within the scopes of the claims are to be embraced by the claims.

What is claimed:

1. A medical gas delivery system, comprising:
- a surface that receives a head of a subject;
- a diffuser on a side of the surface so as to be positioned adjacent to a side of the head of the subject, the diffuser including:
  - a base that supports the diffuser on the surface;
  - a delivery face oriented to face the side of the head of the subject;
  - a recess that opens to the delivery face; and
  - an inlet through which a gas is delivered in communication with the recess;
- a positioner on an opposite side of the surface from the diffuser, the positioner including:
  - a base that supports the positioner on the surface; and
  - an orienting surface that receives a back of the subject's head in a manner that orients the subject's head sideways on the surface and positions the subject's face toward the delivery face of the diffuser; and
- a pillow on which the base of the diffuser and the base of the positioner are positioned and to which the base of the diffuser and the base of the positioner are secured.

2. The medical gas delivery system of claim 1, wherein the delivery face is oriented at an acute angle to the surface.

3. The medical gas delivery system of claim 1, wherein the diffuser further includes:
- a coupler that removably secures the base of the diffuser to the surface.

4. The medical gas delivery system of claim 3, wherein the coupler of the diffuser includes a strap.

5. The medical gas delivery system of claim 3, wherein the coupler of the diffuser comprises a touch fastener.

6. The medical gas delivery system of claim 1, wherein the positioner further includes:
- a coupler that holds the base of the positioner in place on the surface.

7. The medical gas delivery system of claim 6, wherein the coupler of the positioner includes a strap.

8. The medical gas delivery system of claim 6, wherein the coupler of the positioner comprises a touch fastener.

9. A method for delivering a gas to a subject, comprising:
- positioning a positioner at a first location on a surface of a pillow on which a head of a subject will be placed, adjacent to a second location on which the head of the subject will be placed, with an orienting surface of the positioner facing the second location and having a shape that will receive a back of the head of the subject and orient the head of the subject sideways over the second location on the surface;
- positioning a diffuser at a third location on the surface of the pillow on which the head of the subject will be placed, adjacent to the second location and on an opposite side of the second location from the first location, with a delivery face of the diffuser oriented toward the second location so as to deliver the gas to a face of the subject; and
- placing the head of the subject on the second location on the surface, including placing the back of the bead against the orienting surface of the positioner and a side the head against the second location, the face of the subject being oriented toward the delivery face of the diffuser, causing the delivery face of the diffuser to tilt downward in a manner that traps air between the diffuser and the second location on the surface.

10. The method of claim 9, further comprising: delivering the gas through the delivery face of the diffuser to the face of the subject.

11. The method of claim 10, wherein positioning the positioner and positioning the diffuser comprise positioning the positioner and the diffuser on a pillow.

12. The method of claim 9, further comprising: adjusting a lateral position of the diffuser on the surface.

13. The method of claim 9, further comprising: securing the positioner and the diffuser in place on the surface.

14. The method of claim 13, wherein securing comprises securing a base of the positioner and a base of the diffuser to the surface.

15. The method of claim 13, wherein securing comprises placing the positioner in a positioner pocket of a fabric cover over the surface and/or placing the diffuser in a diffuser pocket of the fabric cover over the surface.

16. The method of claim 13, further comprising:

positioning a fabric cover over the positioner, the diffuser, and the surface, including positioning a vent through the fabric cover over or adjacent to the delivery face of the diffuser to enable gas to flow freely from the delivery face of the diffuser to the face of the subject.

17. The method of claim 16, wherein positioning the fabric cover comprises positioning the fabric cover with the vent able to accommodate a plurality of different positions of the diffuser on the surface of the pillow.

18. A method for delivering a gas to a subject, comprising:

positioning a positioner at a first location on a surface of a pillow on which a head of a subject will be placed, adjacent to a second location on which the head of the subject will be placed, with an orienting surface of the positioner facing the second location and having a shape that will receive a back of the head of the subject and orient the head of the subject sideways over the second location on the surface;

positioning a diffuser at a third location on the surface of the pillow on which the head of the subject will be placed, adjacent to the second location and on an opposite side of the second location from the first location, with a delivery face of the diffuser oriented toward the second location so as to deliver the gas to a face of the subject; and securing a base of the positioner and a base of the diffuser to the surface.

19. The method of claim 18, further comprising:

placing the head of the subject on the second location on the surface, including placing the back of the head against the orienting surface of the positioner and a side of the head against the second location, the face of the subject being oriented toward the delivery face of the diffuser.

20. The method of claim 18, wherein:

positioning the positioner and positioning the diffuser comprise positioning the positioner and the diffuser on a pillow; and securing the base of the positioner and the base of the diffuser to the surface comprises securing the base of the positioner and the base of the diffuser to the pillow.

* * * * *